United States Patent [19]
Leibinger et al.

[11] Patent Number: 5,263,980
[45] Date of Patent: Nov. 23, 1993

[54] DEVICE FOR SECURING ARTIFICIAL BODY PARTS, IN PARTICULAR ARTIFICIAL EARS, NOSES AND EYES

[75] Inventors: Karl Leibinger, Tuttlingen-Möhringen; Franz Leibinger, Mühlheim-Stetten, both of Fed. Rep. of Germany

[73] Assignee: Oswald Leibinger GmbH, Muhlheim, Fed. Rep. of Germany

[21] Appl. No.: 629,834

[22] Filed: Dec. 19, 1990

[30] Foreign Application Priority Data

Dec. 22, 1989 [DE] Fed. Rep. of Germany ....... 3942674

[51] Int. Cl.$^5$ .............................. A61F 2/02; A61F 2/28
[52] U.S. Cl. ........................................ 623/11; 623/16; 606/60; 433/172
[58] Field of Search ........................ 623/11, 10, 16, 18; 606/54, 151, 60, 61; 433/171, 172, 173, 174, 175

[56] References Cited

U.S. PATENT DOCUMENTS

| 3,997,138 | 12/1976 | Crock et al. ............................ 606/61 |
| 4,279,248 | 7/1981 | Gabbay ..................................... 606/151 |
| 4,713,003 | 12/1987 | Symington et al. ................. 433/173 |
| 4,796,612 | 1/1989 | Reese ..................................... 606/72 |
| 4,805,602 | 2/1989 | Puno et al. ............................ 128/69 |
| 4,813,967 | 3/1989 | Renard et al. ........................ 623/11 |

FOREIGN PATENT DOCUMENTS

| 1961531 | 12/1959 | Fed. Rep. of Germany . |
| 1075791 | 2/1960 | Fed. Rep. of Germany . |
| 2413883 | 3/1974 | Fed. Rep. of Germany . |
| 2455828 | 11/1974 | Fed. Rep. of Germany . |
| 3812779 | 4/1988 | Fed. Rep. of Germany . |
| 1094558 | 5/1955 | France ................................. 623/10 |
| 1291470 | 10/1972 | United Kingdom . |

*Primary Examiner*—David Isabella
*Attorney, Agent, or Firm*—Schaffer, Robert D.

[57] ABSTRACT

A device for securing artificial body parts, in particular ears, noses and eyes, to a support 12 secured in turn to a bone 10 comprises a post 24 connectable rigidly to the support 12. Rotatably mounted on the post is a rotary member 26 which has a recess 30 for a wire. The artificial body part can be secured to the wire by means of a clamp, clip or the like.

5 Claims, 5 Drawing Sheets

FIG. 2
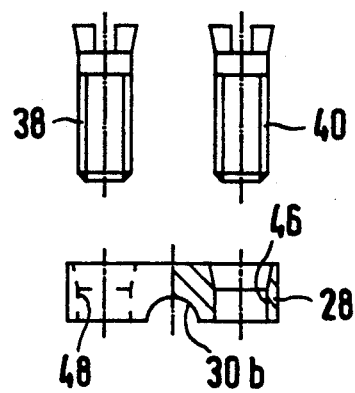
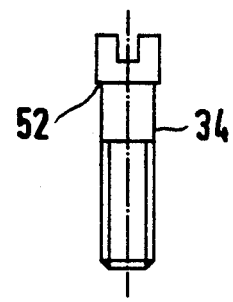
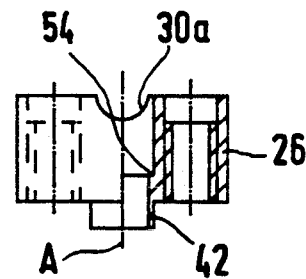
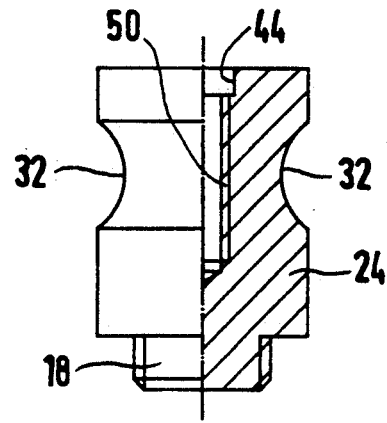

FIG.3
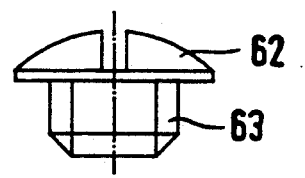
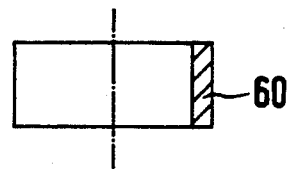
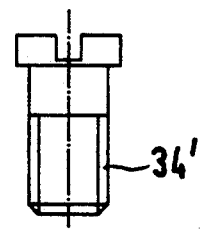
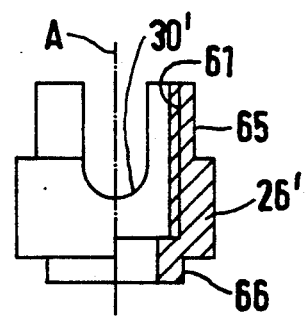
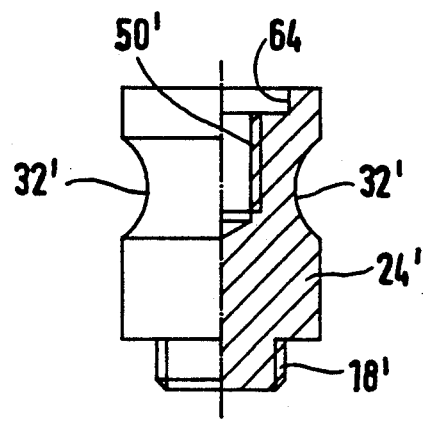

DEVICE FOR SECURING ARTIFICIAL BODY PARTS, IN PARTICULAR ARTIFICIAL EARS, NOSES AND EYES

The invention relates to a device for securing artificial body parts, in particular artificial ears, noses and eyes.

For securing artificial body parts (artificial ears, noses, eyes etc.) in the region of the face, the prior art employs as a rule aids such as ring seats or a prosthesis.

Another solution (DE 19 61 531 A1 and DE 24 13 883 A1) for securing artificial body parts in the region of the face provides that in the cranial bone individual implants are fixed to which the artificial body part is then secured, as with implants in the cavity of the mouth for fixation of dentures. A disadvantage of such an implant system is that adequate bone must be present for the implant posts to be received. It is thus frequently not possible to place the implant posts at the location of the artificial body parts to be secured. Also, such implant posts have the disadvantage that they require a so-called "two-step" procedure, firstly the implant posts being inserted into the bone and remaining there for a relatively long time without loading by the artificial body part so that they can heal. Only thereafter, indeed some months later, is the artificial body part secured to the implant post or posts in a second operation.

Also, such implant systems for securing artificial body parts have the disadvantage that the position and form of the artificial body part cannot always be optimum because on placing the implants unfavourable marginal conditions obtain, i.e. the implants cannot always be placed where they would be desirable for an ideal mounting of the artificial body part.

The invention is based on the problem of providing a device for securing artificial body parts, in particular ears, noses and eyes, to a support which gives the surgeon extensive freedom of configuration, permits a rapid healing process and ensures a reliable and esthetically pleasant fitting of the artificial body part.

According to the invention this problem is solved by a support which is secured to the body bone and can preferably be a grid and on which a post is rigidly mounted on which a rotary member is rotatably secured which comprises a recess for a wire or a web.

The artificial body part (the artificial ear, nose or eye) is then secured to the wire or web by means of such a known clamping device.

It is preferably provided that on said rotary member a cover cap can be secured with which the wire can be clamped to the rotary member so that when using several posts and associated rotary members the entire arrangement including the rotary members is rigid. Before tightening the cover cap the wire or the web and the rotary member are still movable so that the operating surgeon can adapt them on location to the desired geometry.

In a preferred further development of the invention the post comprises an encircling groove for accommodating tissue so that the device as a whole can grow in well.

Preferably, the post comprises at its end facing the support (plate or in particular grid) a threaded pin which is screwable into a corresponding thread in the support.

Hereinafter some examples of embodiment of the invention will be described in detail with the aid of the drawings, wherein:

FIG. 2 shows an example of embodiment of a device for securing the artificial body part to a support in exploded state;

FIG. 3 shows another example of embodiment of a device for securing an artificial body part to a support;

Figure 1:
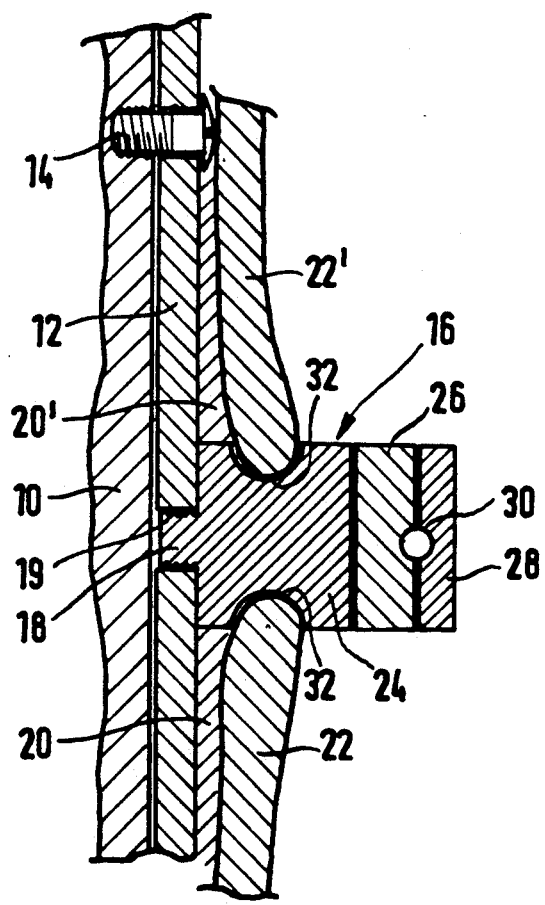
FIG. 1 is a section through a device for securing artificial body parts including a bone piece and a support.
Figure 5:
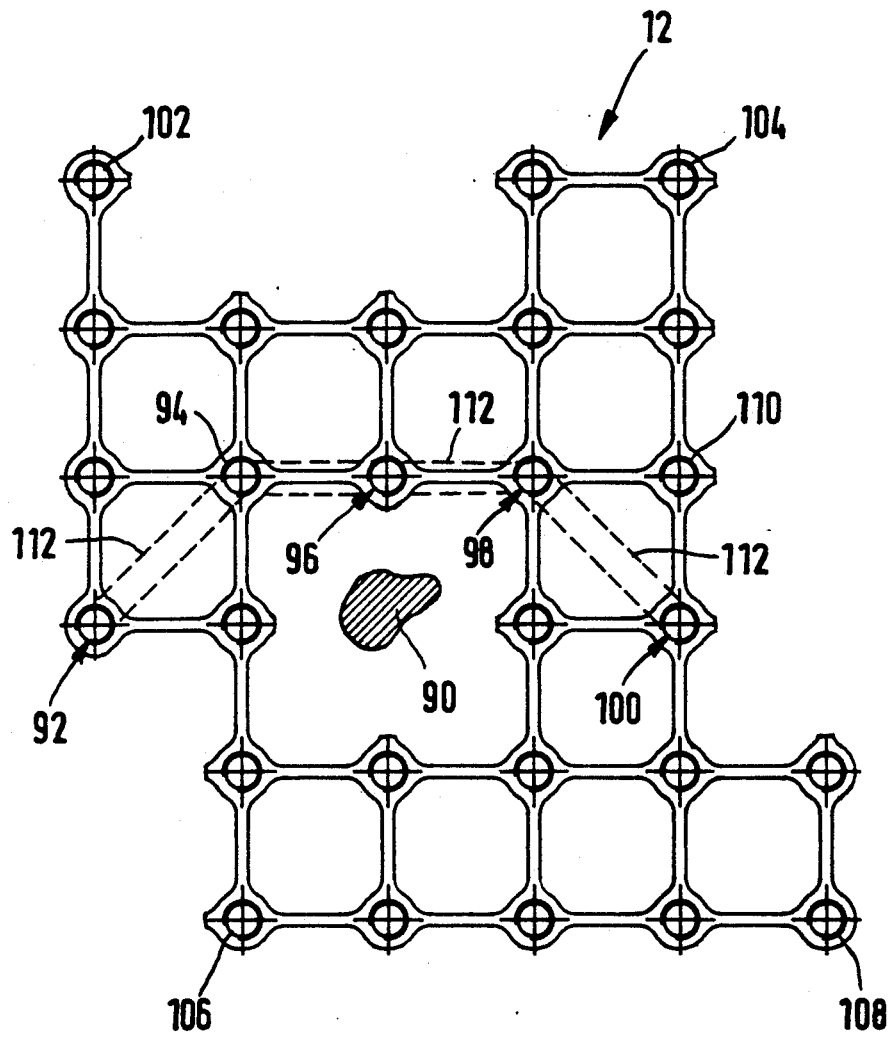

FIG. 1 shows in section a bone piece 10, for example adjacent an auditory canal over which an artificial ear is to be secured. A grid-like support 12 illustrated in more detail in FIG. 5 is secured on the bone 10. The grid-like support 12 comprises a plurality of holes. A screw 14 is lead through one of the holes and screwed into the bone 10. FIG. 1 shows schematically only a single screw 14. In addition, the support 12 is anchored in the bone 10 with several screws as will be explained in further detail below with reference to the example of embodiment according to FIG. 5.

A securing device 16 which is the subject of the invention is secured to the support 12 anchored firmly in the bone 10. The securing device 16 comprises a threaded pin 18 which is screwed into a corresponding thread in a hole 19 in the support 12.

In the healed state bone grows into gaps of the support (cf. FIG. 5) and can partially cover the latter. Such grown bone is indicated by the reference numeral 20 in FIG. 1.

Tissue 22 lies over the support 12 and possibly the bone 20 and on conclusion of the growing-in and healing process encloses the securing device 16.

The securing device 16 comprises a post 24 in which an encircling groove 32 is formed into which the tissue 22, 22' densely grows. The post 24 is screwed firmly into the support 12 by means of the threaded pin 18, i.e. cannot move with respect to said support, in particular not turn.

A rotary member 26 is secured to the post 24 in such a manner that it is initially rotatable with respect to the post 24 about the common longitudinal axis of the parts. Mounted over the rotary member 26 is a cover cap 28. In the rotary member 26 and the cover cap 28 a through recess 30 is formed for receiving a wire. The function of the wire will be explained in detail below with reference to FIG. 5.

Figure 4:
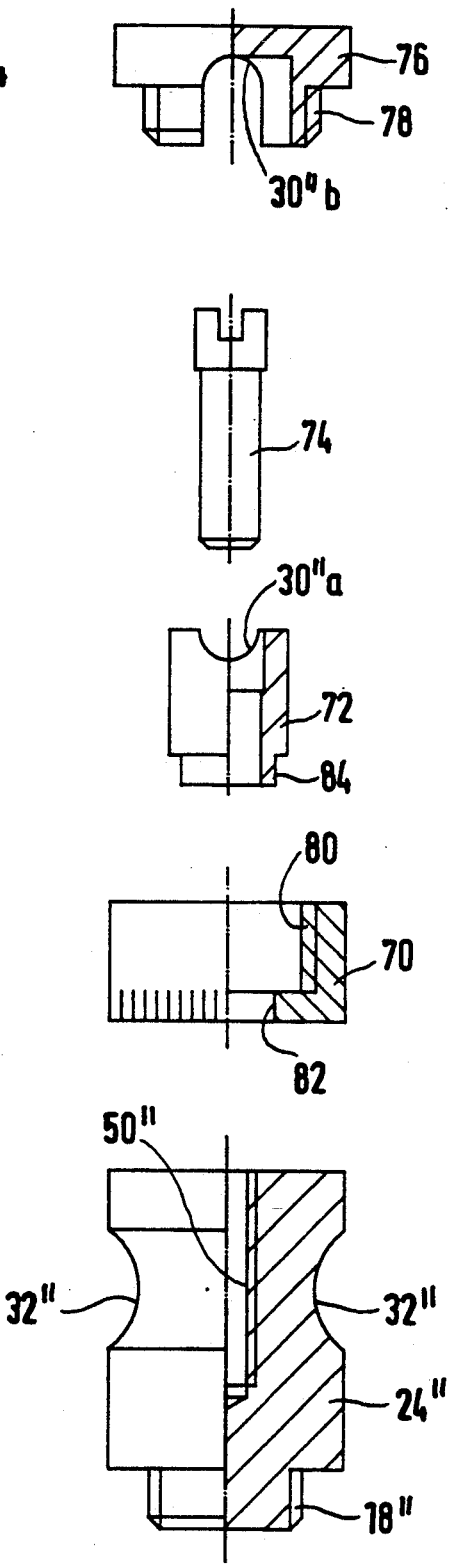
FIG. 4 shows a further example of embodiment of a device for securing an artificial body part to a support and FIG. 5 shows a support in plan view.

FIGS. 2, 3 and 4 show various examples of embodiment for a securing device 16.

In the example of embodiment according to FIG. 2 the rotary member 26 is secured to the post 24 by means of a screw 34 so that it is rotatable about the longitudinal axis A of the parts. By means of screws 38, 40 the cover cap 28 is secured to the rotary member 26. In the assembled state the screw 34 is sunk into the rotary member 26 to such an extent that the recess 30a remains free, i.e. the head of the screw 34 does not project into the recess 30a.

At its lower end the rotary member 26 comprises a projection 42 which fits into a complementary recess 44 in the post 24 so that the rotary member 26 can turn freely with respect to the post 24.

The screws 38, 40 pass through bores 46 and 48 respectively in the cover cap 28.

The length of a bore 50 in the post 24, the height of the rotary member 26 and the length of the screw 34 are so dimensioned that in the assembled state a stop 52 on the head of the screw 34 is located directly above a corresponding stop 54 in the rotary member 26 in such a manner that said rotary member 26 can execute a rotational movement but cannot move in the direction of the longitudinal axis A.

In the cover cap 28 a likewise semicircular recess 30b corresponding to the recess 30a in the rotary member 26 is formed so that in the assembled state all together a recess according to FIG. 1 of substantially circular section results in which a wire or web can be first loosely positioned and after tightening of the screws 38, 40 can be rigidly connected to the rotary member 26.

FIG. 3 shows a further example of embodiment of a securing device 16.

In the example of embodiment according to FIG. 3 components corresponding to the example of embodiment according to FIG. 2 are provided with the same reference numerals which additionally have an apostrophe.

The rotary number 26' projects with a projection 66 into a complementary recess 64 in the post 24'. A screw 34' engages through the rotary member 26' and is screwed into a bore 50' in the post 24'. The rotary member 26' remains free to rotate about the axis A.

A sleeve 60 fits over a tapered portion 65 of the rotary member 26'. A screw 62 passes through the sleeve 60 and with an external thread 63 can be screwed into an internal thread 61 of the tapered portion 65. On tightening of the screw 62 with respect to the rotary member 26' a wire arranged in the recess 30' can be clamped by means of the sleeve 60.

FIG. 4 shows a modification of a securing device 16 (FIG. 1). In the example of embodiment according to FIG. 4 components corresponding to the example of embodiment according to FIG. 2 are provided with the same reference numerals each having two apostrophes.

Via a post 24' a sleeve 70 is secured by means of a screw 74 which engages through a rotary member 72 and is screwed into a corresponding bore 50" in the post 24". The rotary member 72 engages with a projection 84 into a corresponding recess 82 in the sleeve 70. In the assembled state the recess 30"a is free, i.e. the head of the screw 74 is sunk into the rotary member 72. A cap 76 is provided with an external thread 78 cooperating with an internal thread 80 in the sleeve 70. For this purpose the sleeve 70 is provided on the outside with a knurling so that by turning the sleeve 70 with respect to the cap 76 the latter can be tightened. When this is done a wire or web placed into the recesses 30"a in the rotary member 72 and 30"b in the cap 76 can be clamped.

FIG. 5 shows a plan view of a support 12 of which only a fragment is shown in FIG. 1.

The support 12 is made grid-like and at each of the positions 92, 94, 96, 98 and 100 securing devices 16 according to FIGS. 1 to 4 are mounted.

At each of the positions 102, 104, 106, 108 and 110 the grid-like support 12 is secured with a screw 15 (cf. FIG. 1) to the bone 10. By means of the support 12 shown in FIG. 5 an artificial ear for example is to be secured above an auditory canal 90. For this purpose a wire 112 is secured through the recesses 30 in the individual securing devices 16 (at said position 92, 94, 96, 98 and 100). Due to the rotatability of the rotary members described above the wire can first be inserted by the surgeon and then bent as desired to form a wire network or web. Thereafter, the fixing of the wire described above with respect to the rotary members may be effected so that finally a three-dimensionally stable arrangement is achieved. The artificial ear can then be secured with clamps to the wire 112 in known manner.

We claim:

1. An implant system including a biocompatible device for securing an artificial body part, in particular an artificial eye, nose, or ear, to a support secured to a bone, comprising:
   a post having means for rigidly connecting said post to said support;
   a rotary member having means for being mounted onto said post so as to allow for rotation of said rotary member with respect to said post in the assembled state of the device about a common longitudinal axis of said post and said rotary member but not to allow for axial movement of said rotary member in the direction of said longitudinal axis;
   a recess in said rotary member for receiving a wire; and
   means for clamping said wire in said recess.

2. An implant system including a biocompatible device for securing an artificial body part, in particular an artificial eye, nose, or ear, to a support secured to a bone, comprising:
   a post having means for rigidly connecting said post to said support, wherein said post comprises a groove about said post for accommodating tissue;
   a rotary member having means for being mounted onto said post so as to allow for rotation of said rotary member with respect to said post about a common longitudinal axis of said post and said rotary member but not to allow for axial movement of said rotary member in the direction of said longitudinal axis;
   a recess in said rotary member for receiving a wire; and
   means for clamping said wire in said recess.

3. An implant system including a biocompatible device for securing an artificial body part, in particular an artificial eye, nose, or ear, to a support secured to a bone, comprising:
   a post having means for rigidly connecting said post to said support, wherein said means for rigidly connecting said post to said support comprises a threaded pin;
   a rotary member having means for being mounted onto said post so as to allow for rotation of said rotary member with respect to said post about a common longitudinal axis of said and said rotary member but not to allow for axial movement of said rotary member in the direction of said longitudinal axis;
   a recess in said rotary member for receiving a wire; and
   means for clamping said wire in said recess.

4. An implant system including a biocompatible device for securing an artificial body part, in particular an artificial eye, nose, or ear, to a support secured to a bone, comprising:
   a post having means for rigidly connecting said post to said support, wherein said support is a grid comprising threaded holes, and wherein said post includes a threaded pin for securing said post to said grid by screwing said pin into a threaded hole of said grid;

a rotary member having means for being mounted onto said post so as to allow for rotation of said rotary member respect to said post about a common longitudinal axis of said post and said rotary member but not to allow for axial movement of said rotary member in the direction of said longitudinal axis;

a recess in said rotary member for receiving a wire; and means for clamping said wire in said recess.

5. The device of claims 1, 2, 3, or 4, wherein said means for clamping said wire in said recess comprises a cover cap which is secured to said rotary member.

* * * * *